(12) United States Patent
Tobin, Jr. et al.

(10) Patent No.: US 8,243,999 B2
(45) Date of Patent: Aug. 14, 2012

(54) METHOD AND SYSTEM FOR THE DIAGNOSIS OF DISEASE USING RETINAL IMAGE CONTENT AND AN ARCHIVE OF DIAGNOSED HUMAN PATIENT DATA

(75) Inventors: Kenneth William Tobin, Jr., Harriman, TN (US); Thomas P. Karnowski, Knoxville, TN (US); Edward Chaum, Memphis, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 1165 days.

(21) Appl. No.: 11/416,834

(22) Filed: May 3, 2006

(65) Prior Publication Data

US 2007/0258630 A1    Nov. 8, 2007

(51) Int. Cl.
G06K 9/00    (2006.01)
(52) U.S. Cl. ......................................................... 382/115
(58) Field of Classification Search .................. 382/115, 382/117, 128, 305; 351/205–221; 396/118, 396/51; 600/318–321
See application file for complete search history.

(56) References Cited

U.S. PATENT DOCUMENTS

| | | | | |
|---|---|---|---|---|
| 5,233,517 A | * | 8/1993 | Jindra | 600/558 |
| 5,270,924 A | * | 12/1993 | Hideshima | 382/117 |
| 5,579,471 A | * | 11/1996 | Barber et al. | 715/700 |
| 5,868,134 A | * | 2/1999 | Sugiyama et al. | 600/300 |
| 5,878,746 A | * | 3/1999 | Lemelson et al. | 600/407 |
| 5,911,139 A | * | 6/1999 | Jain et al. | 707/3 |
| 6,053,865 A | * | 4/2000 | Sugiyama et al. | 600/300 |
| 6,104,828 A | * | 8/2000 | Shioiri | 382/128 |
| 6,115,489 A | * | 9/2000 | Gupta et al. | 382/141 |
| 6,285,995 B1 | * | 9/2001 | Abdel-Mottaleb et al. | 707/3 |
| 6,292,577 B1 | * | 9/2001 | Takahashi | 382/128 |

(Continued)

FOREIGN PATENT DOCUMENTS

EP    990997 A1 *    4/2000

OTHER PUBLICATIONS

Goldbaum, M.; Moezzi, S.; Taylor, A.; Chatterjee, S.; Boyd, J.; Hunder, E.; Jain, R., "Autmated Diagnosis and Image Understanding with Object Extraction, Object Classification, and Inferencing in Retinal Images," 1996, IEEE, International Conference on Image Processsing Proceedings, vol. 3, pp. 695-698.*

(Continued)

*Primary Examiner* — Vikkram Bali
(74) *Attorney, Agent, or Firm* — Novak Druce + Quigg LLP

(57) ABSTRACT

A method for diagnosing diseases having retinal manifestations including retinal pathologies includes the steps of providing a CBIR system including an archive of stored digital retinal photography images and diagnosed patient data corresponding to the retinal photography images, the stored images each indexed in a CBIR database using a plurality of feature vectors, the feature vectors corresponding to distinct descriptive characteristics of the stored images. A query image of the retina of a patient is obtained. Using image processing, regions or structures in the query image are identified. The regions or structures are then described using the plurality of feature vectors. At least one relevant stored image from the archive based on similarity to the regions or structures is retrieved, and an eye disease or a disease having retinal manifestations in the patient is diagnosed based on the diagnosed patient data associated with the relevant stored image(s).

20 Claims, 4 Drawing Sheets

U.S. PATENT DOCUMENTS

| | | | |
|---|---|---|---|
| 6,306,087 B1* | 10/2001 | Barnhill et al. | 600/300 |
| 6,415,173 B1* | 7/2002 | Sponsel et al. | 600/407 |
| 6,523,954 B1* | 2/2003 | Kennedy et al. | 351/205 |
| 6,535,776 B1 | 3/2003 | Tobin, Jr. et al. | |
| 6,556,853 B1* | 4/2003 | Cabib et al. | 600/407 |
| 6,560,476 B1* | 5/2003 | Pelletier et al. | 600/410 |
| 6,678,703 B2* | 1/2004 | Rothschild et al. | 707/201 |
| 6,690,828 B2* | 2/2004 | Meyers | 382/218 |
| 6,751,343 B1 | 6/2004 | Ferrell et al. | |
| 6,751,363 B1* | 6/2004 | Natsev et al. | 382/305 |
| 6,891,920 B1* | 5/2005 | Minyard et al. | 378/37 |
| 6,925,199 B2* | 8/2005 | Murao | 382/131 |
| 6,934,698 B2* | 8/2005 | Judd et al. | 707/1 |
| 6,993,161 B2* | 1/2006 | Marshall et al. | 382/117 |
| 6,996,260 B1* | 2/2006 | Skands et al. | 382/128 |
| 7,027,633 B2* | 4/2006 | Foran et al. | 382/133 |
| 7,031,555 B2* | 4/2006 | Troyanker | 382/305 |
| 7,043,474 B2* | 5/2006 | Mojsilovic et al. | 707/6 |
| 7,110,582 B1* | 9/2006 | Hay | 382/128 |
| 7,187,786 B2* | 3/2007 | Kee | 382/118 |
| 7,220,000 B2* | 5/2007 | Alster et al. | 351/224 |
| 7,228,006 B2* | 6/2007 | Stubler et al. | 382/286 |
| 7,244,230 B2* | 7/2007 | Duggirala et al. | 600/300 |
| 7,310,651 B2* | 12/2007 | Dave et al. | 707/104.1 |
| 7,374,077 B2* | 5/2008 | Shimura | 235/375 |
| 7,458,936 B2* | 12/2008 | Zhou et al. | 600/437 |
| 7,474,775 B2* | 1/2009 | Abramoff et al. | 382/128 |
| 7,483,919 B2* | 1/2009 | Galperin | 707/104.1 |
| 7,500,751 B2* | 3/2009 | Tajima et al. | 351/206 |
| 7,515,754 B2* | 4/2009 | Hung | 382/218 |
| 7,524,064 B2* | 4/2009 | Wyatt | 351/211 |
| 7,575,321 B2* | 8/2009 | Newman et al. | 351/205 |
| 7,672,976 B2* | 3/2010 | Tobin et al. | 707/104.1 |
| 2001/0043729 A1* | 11/2001 | Giger et al. | 382/128 |
| 2002/0021828 A1* | 2/2002 | Papier et al. | 382/128 |
| 2002/0039434 A1* | 4/2002 | Levin et al. | 382/128 |
| 2002/0052551 A1* | 5/2002 | Sinclair et al. | 600/476 |
| 2003/0026470 A1* | 2/2003 | Kasai | 382/132 |
| 2003/0071970 A1* | 4/2003 | Donnerhacke et al. | 351/221 |
| 2003/0095692 A1* | 5/2003 | Mundy et al. | 382/128 |
| 2003/0103663 A1* | 6/2003 | Li et al. | 382/131 |
| 2003/0229278 A1* | 12/2003 | Sinha | 600/407 |
| 2004/0003001 A1* | 1/2004 | Shimura | 707/104.1 |
| 2004/0024758 A1* | 2/2004 | Iwasaki | 707/3 |
| 2004/0071368 A1* | 4/2004 | Chadha et al. | 382/305 |
| 2004/0085542 A1* | 5/2004 | Soliz et al. | 356/456 |
| 2004/0101177 A1* | 5/2004 | Zahlmann et al. | 382/128 |
| 2004/0105074 A1* | 6/2004 | Soliz et al. | 351/206 |
| 2004/0151379 A1* | 8/2004 | Kim et al. | 382/209 |
| 2005/0021512 A1* | 1/2005 | Koenig | 707/3 |
| 2005/0038678 A1* | 2/2005 | Qian et al. | 705/2 |
| 2005/0057721 A1* | 3/2005 | Kolanko et al. | 351/205 |
| 2005/0094099 A1* | 5/2005 | Newman et al. | 351/205 |
| 2005/0171974 A1* | 8/2005 | Doering | 707/104.1 |
| 2005/0210015 A1* | 9/2005 | Zhou et al. | 707/3 |
| 2006/0112092 A1* | 5/2006 | Ziou et al. | 707/5 |
| 2006/0147099 A1* | 7/2006 | Marshall et al. | 382/128 |
| 2007/0003117 A1* | 1/2007 | Wheeler et al. | 382/128 |
| 2007/0019846 A1* | 1/2007 | Bullitt et al. | 382/128 |
| 2007/0081699 A1* | 4/2007 | Avinash et al. | 382/128 |
| 2007/0081700 A1* | 4/2007 | Blumenfeld et al. | 382/128 |
| 2007/0081701 A1* | 4/2007 | Sirohey et al. | 382/128 |
| 2007/0127795 A1* | 6/2007 | Lau et al. | 382/128 |

OTHER PUBLICATIONS

Gupta, A.; Moezzi, S.; Taylor, A.; Chatterjee, S.; Jain, R.; Goldbaum, M.; Burgess, S., "Content-Based Retrieval of Opthalmological Images," 1996, IEEE, Proceedings, International Conference on Image Processing, vol. 3, pp. 703-706.*

Goldbaum, M.; Katz, N.; Chaudhuri, S.; Nelson, M., "Image Understanding for Automated Retinal Diagnosis," 1989, SCAMC, Proceedings: The Thirteenth Annual Symposium on Computer Applications in Medical Care, pp. 756-760.*

* cited by examiner

METHOD AND SYSTEM FOR THE DIAGNOSIS OF DISEASE USING RETINAL IMAGE CONTENT AND AN ARCHIVE OF DIAGNOSED HUMAN PATIENT DATA

STATEMENT REGARDING FEDERALLY SPONSORED RESEARCH OR DEVELOPMENT

The United States Government has rights in this invention pursuant to contract no. DEAC05-00OR22725 between the United States Department of Energy and UT-Battelle, LLC.

CROSS-REFERENCE TO RELATED APPLICATIONS

N/A

FIELD OF THE INVENTION

The invention relates to automated methods for diagnosing retinal pathologies and other medical abnormalities.

BACKGROUND

The World Health Organization estimates that 135 million people have diabetes mellitus worldwide and that the number of people with diabetes will increase to 300 million by the year 2025. More than 18 million Americans currently have diabetes and the number of adults with the disease is projected to more than double by the year 2050. An additional 16 million adults between the ages of 40-74 have pre-diabetes and are at high risk for developing diabetes. Visual disability and blindness have a profound socioeconomic impact upon the diabetic population and diabetic retinopathy (DR) is the leading cause of new blindness in working-age adults in the industrialized world. The prevalence rates for DR and vision-threatening DR in adults over age 40 is 40.3% and 8.2%, respectively. It is estimated that as much as $167 million dollars and 71,000-85,000 sight-years could be saved annually in the US alone with improved screening methods for diabetic retinopathy.

The current methods used to address screening for DR relies on either a patient visit to a physician specifically trained to diagnose eye disease from digital retinal photography, or the use of established retinal reading centers such as the Joslin Vision Network (Boston, Mass.), and Inoveon Corp. (Oklahoma City, Okla.). While reading centers have shown that digital photography is an effective tool for identifying DR when performed by experienced, certified readers, the turn-around time for a diagnosis is roughly 72 hours (3 days) on average. What is needed is an automated diagnosis system that is self-contained and provides very rapid turn-around, with minimal or no dependency on human interpreters.

SUMMARY OF THE INVENTION

A method for diagnosing medical conditions having retinal manifestations includes the steps of providing a content-based image retrieval (CBIR) system including an archive of stored digital retinal photography images and diagnosed patient data corresponding to the retinal photography images, the stored images each indexed in a CBIR database using a plurality of feature vectors, the feature vectors corresponding to distinct descriptive characteristics of the stored images. A query image of the retina of a patient obtained. Using image processing, regions or structures are then identified in the query image. The regions or structures are described using the plurality of feature vectors. At least one relevant stored image from the archive based on similarity to the regions or structures is identified. A disease having retinal manifestations in the patient is then diagnosed based on the diagnosed patient data associated with the retrieved relevant stored image(s).

The query image of the retina of the patient generally includes vascular arcades, the macula and optic disc, and surrounding regions. The regions or structures identified using image processing preferably include both normal physiologic and anomalous pathologic regions or structures.

The medical conditions having retinal manifestations diagnosed can comprises eye diseases, or a variety of non-eye disease which have retinal manifestations. Eye diseases diagnosable using the invention include, but are not limited to, common diseases of the optic nerve and macula, such as glaucoma and age-related macular degeneration.

The anomalous regions can be selected based on one or more of spectral content, textures, structures, and shapes. The identifying step can comprise imposing a macular coordinate system such that the spatial positioning of disease-based morphological changes or location of lesions is described in relation to a position of the macula and the optic disc. The database can include non-image data other than the diagnosed patient data, selected from the group consisting of age, race, gender, and medical history data for the patient.

The feature vectors are preferably indexed using an unsupervised clustering method into a hierarchical search tree. Diagnosed patient data can be provided by a retinal professional. The method can be entirely automatic. The obtaining step can comprise automatically locating the optic disc and macula regions, imposing a macular coordinate system after automatic localization of a center of the macula in the image, and describing spatial positioning of disease-based morphological changes in relation to a position of the macula and optic disc.

At least a portion of the digital retinal photography images comprising the archive can be obtained at a remote location. For example, the Internet can be used to provide digital retinal photography images obtained from the remote location.

In one embodiment of the invention, the method further comprises the step of increasing information content for the CBIR database, wherein the increasing information content step comprises the steps of calculating a visual similarity parameter value based on a degree of visual similarity between feature vectors of an incoming image being considered for entry into the database and feature vectors of a most similar of the plurality of stored images in the associated system, and determining whether to store or how long to store the feature vectors associated with the incoming image in the database based on the visual similarity parameter value. The visual similarity parameter can be based on a Euclidean distance or an L-norm distance. The method can further comprise the step of defining a threshold value, wherein if the visual similarity parameter value is above the threshold value the feature vectors of the incoming image is denied entry into the database, and if the similarity parameter value is less than the threshold the feature vectors of the incoming image is entered into the database.

In one embodiment of the invention, the archive of digital retinal photography images includes retinal images of the patient, the method comprising the steps of comparing the query image to retinal images of the patient in the archive, and assessing the progression of the disease for the patient.

A content-based image retrieval (CBIR) system for diagnosing diseases having retinal manifestations comprises a computer apparatus programmed with a routine set of instructions stored in a fixed medium, the computer apparatus comprising a CBIR database including a historical database comprising diagnosed patient data corresponding to an archive of digital retinal photography images. The images are each indexed in the database using a plurality of feature vectors, the feature vectors corresponding to distinct descriptive characteristics of the images. The system also includes structure for obtaining a query image of the retina of a patient, structure to identify using image processing regions or structures in the query image, structure for describing the regions or structures using the plurality of feature vectors, structure for retrieving at least one relevant stored image from the archive based on similarity to the regions or structures, and structure for diagnosing a disease having retinal manifestations in the patient based on diagnosed patient data associated with the relevant stored images. The system preferably further comprises structure for implementing a clustering method to index the feature vectors in a hierarchical search tree.

BRIEF DESCRIPTION OF THE DRAWINGS

A fuller understanding of the present invention and the features and benefits thereof will be accomplished upon review of the following detailed description together with the accompanying drawings, in which.

DETAILED DESCRIPTION OF THE INVENTION

Figure 1:
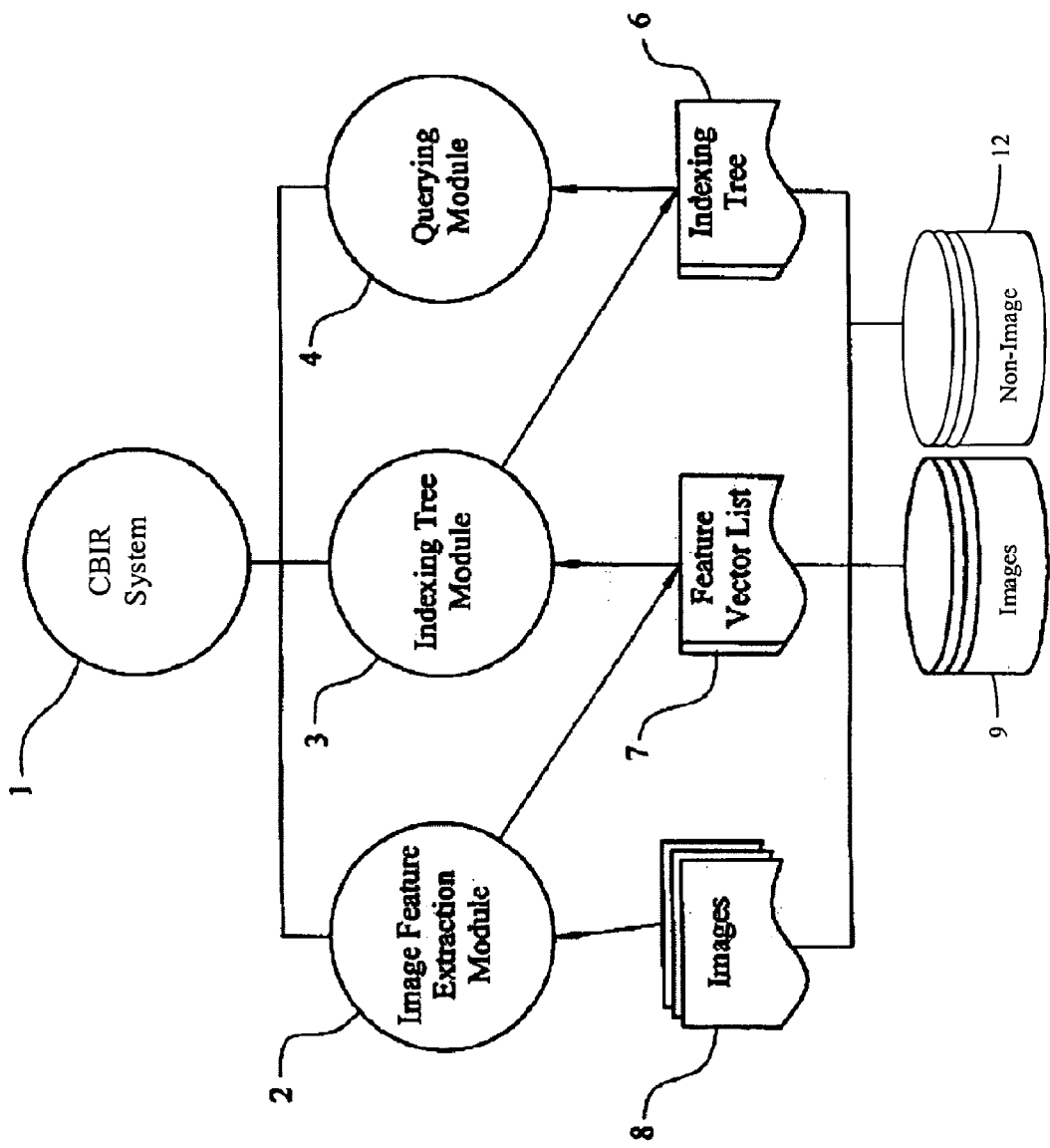
FIG. 1 is a schematic representation of an exemplary computer-based CBIR system according to an embodiment of the invention.

A method for diagnosing medical conditions having retinal manifestations, including retinal pathologies, includes the steps of providing a content based image retrieval (CBIR) historical database including indexed retinal images and non-image data including diagnosed patient data. CBIR generally refers to the field of study, methods, and technology used to index a large population of images so that they can be ordered and retrieved based on visual content in an efficient manner. Visual content is typically described in terms of the color (i.e., spectral content), textures, structures, and shapes of the imagery or of particular regions within the imagery. In a preferred embodiment, non-image data in addition to the diagnosed patient data corresponding each image is provided, such as age, race, gender, and other medical history data for the patient (or the family of the patient).

The images stored in the CBIR system are each indexed using a plurality of feature vectors, the feature vectors corresponding to distinct descriptive characteristics of the images. The feature vectors comprise the indices for the images in the system. The feature vectors extracted from an image become the index for that image in the database, typically being a unique identifier for that image. The indices are stored in a table in the CBIR database, usually along with a pointer to the location of the image residing in a storage media (e.g. hard drive).

A query image of the retina of a patient for diagnosis is obtained that generally includes the macula and optic disc, and surrounding regions. Using image processing normal physiologic and anomalous regions or structures in the query image can be identified. The anomalous regions are described using the plurality of feature vectors. Following a query of the records stored in the database, at least one relevant stored image is retrieved from the database based on similarity to the anomalous regions. A diagnosis for the patient for eye diseases and non-eye diseases having retinal manifestations is then rendered based on the diagnosed patient data associated with the relevant stored image(s).

The invention can be used to diagnose a variety of eye diseases. Eye diseases can include, but are not limited to, common diseases of the optic nerve and macula, such as glaucoma and age-related macular degeneration. However, the invention is not limited to diagnosing eye diseases since many non-eye diseases and medical conditions have retinal manifestations.

Many systemic non-eye diseases have specific and significant retinal manifestations. Such manifestations processed according to the invention can aid in the diagnosis, either alone, or in conjunction with other measurements. Examples of medical conditions having associated retinal manifestations include hypertension, systemic vasculitides (such as lupus, oculo-arthropathies), coagulopathies, embolic diseases, infectious diseases of the blood and brain (endocarditis, toxoplasmosis, syphillis etc), leukemia, lymphoma and metastatic diseases to the eye, congenital malformations of the brain, genetic or acquired systemic diseases that include ocular manifestations, such as von Hippel Lindau or tuberous sclerosis.

FIG. 1 illustrates a diagnostic CBIR system 1 in accordance with one inventive arrangement. The diagnostic CBIR system 1 includes storage media 9 having stored therein a collection of retinal images indexed as feature vectors in associated feature vector list 7 which stores descriptive data corresponding to each stored image. System 1 also preferably includes non-image storage 12 for storing non-image information comprising diagnosed patient data, along other non-image data, such as age, race, gender, and other medical history data for the patient (or history of the family of the patient).

System 1 includes three basic modules, an image feature extraction module 2, an indexing module 3, and a querying module 4, with each module performing a different CBIR function.

First, the image feature extraction module 2 can represent query image and database images 8 in terms of a small number of numerical descriptors. Specifically, the image feature extraction module 2 can receive as an input, retinal image 8. The image feature extraction module 2 can survey the image 8 deriving a vector of numerical descriptors corresponding to the image 8. In a preferred embodiment as disclosed in U.S. Pat. No. 6,751,343 to Ferrel et al entitled "Method for indexing and retrieving manufacturing-specific digital imagery based on image content", unlike prior CBIR systems, the manufacturing imagery can be described in terms of a plurality of independent sets of characteristics, such as image modality and overall characteristics, substrate-background characteristics, and anomaly-defect characteristics. Ferrel et al. is incorporated by reference into the present application in its entirety.

Moreover, the characteristics used to describe the modality, background, and defect are based on the texture, color, and shape of the image or image structures. In a retinal diagnostics embodiment these characteristics describe modality, physiologic structure such as the characteristics of the optic nerve, macula region and vascular arcades, and the structures associated with pathology from lesions, hemorrhages, and edema. In the preferred embodiment, the image feature extraction module 2 pre-processes every image to generate a series of feature vectors having these descriptive set of features, each vector weighted to a particular characteristic of the stored image. Subsequently, the image feature extraction module 2 can store each of the series of vectors in a corresponding feature vector list 7.

The second module forming the diagnostic CBIR system 1, an indexing module 3, can generate a series of hierarchical search trees to generate an hierarchical search/indexing tree 6, each binary search hierarchical search tree corresponding to a particular characteristic of a stored image. Specifically, the indexing module 3 can read a vector of numerical descriptors contained in a particular feature vector list 7, the vector corresponding to a stored image. Subsequently, preferably using an unsupervised clustering method, the indexing module 3 can create and insert a node containing the vector into a hierarchical search tree 6 keyed on the same image characteristic as the feature vector list 7. The indexing module 3 can perform the node insertion operation for each feature vector list 7 stored. Thus, each resulting hierarchical search tree 6 can provide for the rapid location of candidate imagery stored in storage media 9, each hierarchical search tree 6 weighted to a particular image characteristic.

The third module forming the diagnostic CBIR system 1, a querying module 4, can accept a query image from a user and can return to the user, a collection of similar images stored in storage media 9. Specifically, the querying module 4 can perform an appropriate first level data reduction based upon the query image's associated vectors. Significantly, the image feature extraction module 2, using the query image as an input, can generate the associated feature vectors. Using the feature vector numerical descriptors as a guideline, a very rapid traversal of indexing tree 6 in the first-level data reduction routine can produce a preliminary selection of matching images stored in storage media 9. Subsequently, a relevance feedback routine contained within the querying module 4 can receive input from the user to further focus the image search to the most relevant images. In particular, in a preferred embodiment the user can select several images contained in the preliminary selection of matching images, the selected images having similar characteristics to the query image. Following the relevance feedback procedure, a second level data reduction can be performed using the relevance feedback. Once the system has produced a reduced set of image descriptions, each image can be combined to provide the user of system 1 with a vastly reduced set of images having similar characteristics to the query image.

Although the present invention shares certain basic details with Ferrel et al., there are significant and non-obvious details specific to the implementation of the present invention that are unique to DR. For example, the methods for extracting retinal structures, such as the optic nerve, macula, vasculature, and the variety of lesions present, and for describing these structures, such as the statistical features used, are very different from the semiconductor or other manufacturing-based defect case disclosed in Ferrel et al. Also, the present invention uses non-image derived data, such as disease states to automatically infer and present a description of pathology to the user. In one embodiment the disease states are put forth by the Preferred Practice Patterns of the American Academy of Opthalmology (AAO, 2003), the disease states are assigned by a retinal professional (expert), such as an opthalmologist, and stored along with the historical retinal image database.

The computer diagnosis method according to the invention is generally implemented on a high speed computer system. The system includes memory (preferably non-volatile memory) which stores the historical database containing diagnosed patient data in a large archive of digital retinal photography.

Figure 2:
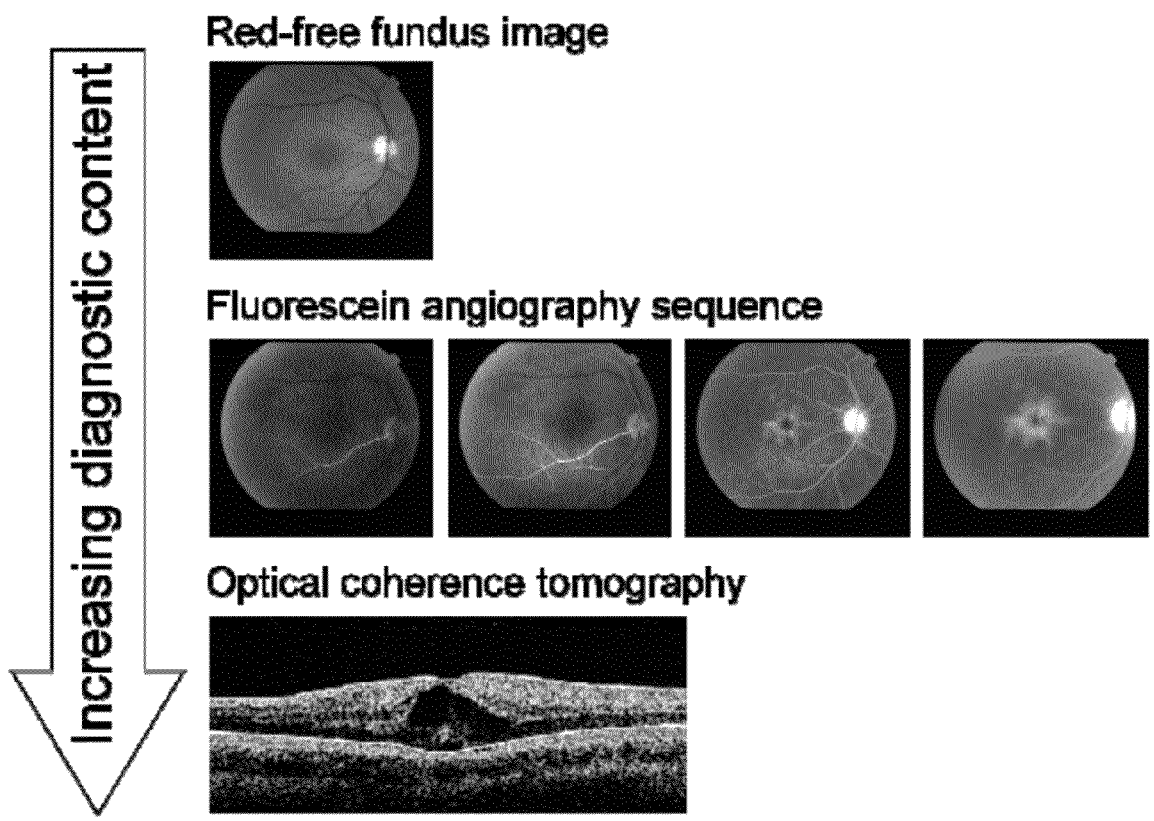
FIG. 2 shows scanned images of a retina presented in three (3) different levels of diagnostic content. The diagnostic content in increasing order is the red-free fundus imagery (top image), fluorescein angiography sequences (center images), and optical coherent tomography (OCT) retinal cross-sections (bottom image). Each successive mode of data, contains more descriptive image content suitable for automated diagnosis, but is more expensive and/or complex to gather.

FIG. 2 shows scanned images of a retina presented in three (3) different levels of diagnostic content. The exemplary diagnostic content is in increasing order the red-free fundus imagery (top image), fluorescein angiography sequences (center images), and optical coherent tomography (OCT) retinal cross sections (bottom image). As noted above, the retinal image data associated with the patient is preferably stored along non-image data, comprising diagnostic data and other non-image data including age, race, gender, and other medical history data for the patient. Each patient's record diagnostic data record stored in the archive preferably includes a description of the prevalent pathology at two levels, such as the two levels described below.

In a preferred embodiment, the record contains a general two level characterization of the disease state, such as put forth by the Preferred Practice Patterns of the American Academy of Opthalmology (AAO, 2003) as follows:
  1. No Retinopathy
  2. Mild Retinopathy
  3. Moderate Retinopathy
  4. Moderate to Severe Retinopathy
  5. Severe Retinopathy
  6. Proliferative Retinopathy The patient record preferably also has a further detailed description of their particular pathology according to:
  Presence of neovascular variation of the optic disc,
  Presence of microaneurysms and retinal hemorrhages,
  Presence of drusen,
  Presence of exudates,
  Presence of cotton-wool spots, and,
  the locations of these events relative to the fovea and optic nerve.
  In addition,
  Presence or absence of clinically significant macular edema and its size and location relative to the fovea (of significance in assessing the severity of disease and risk of vision loss in each eye).

Figure 3:
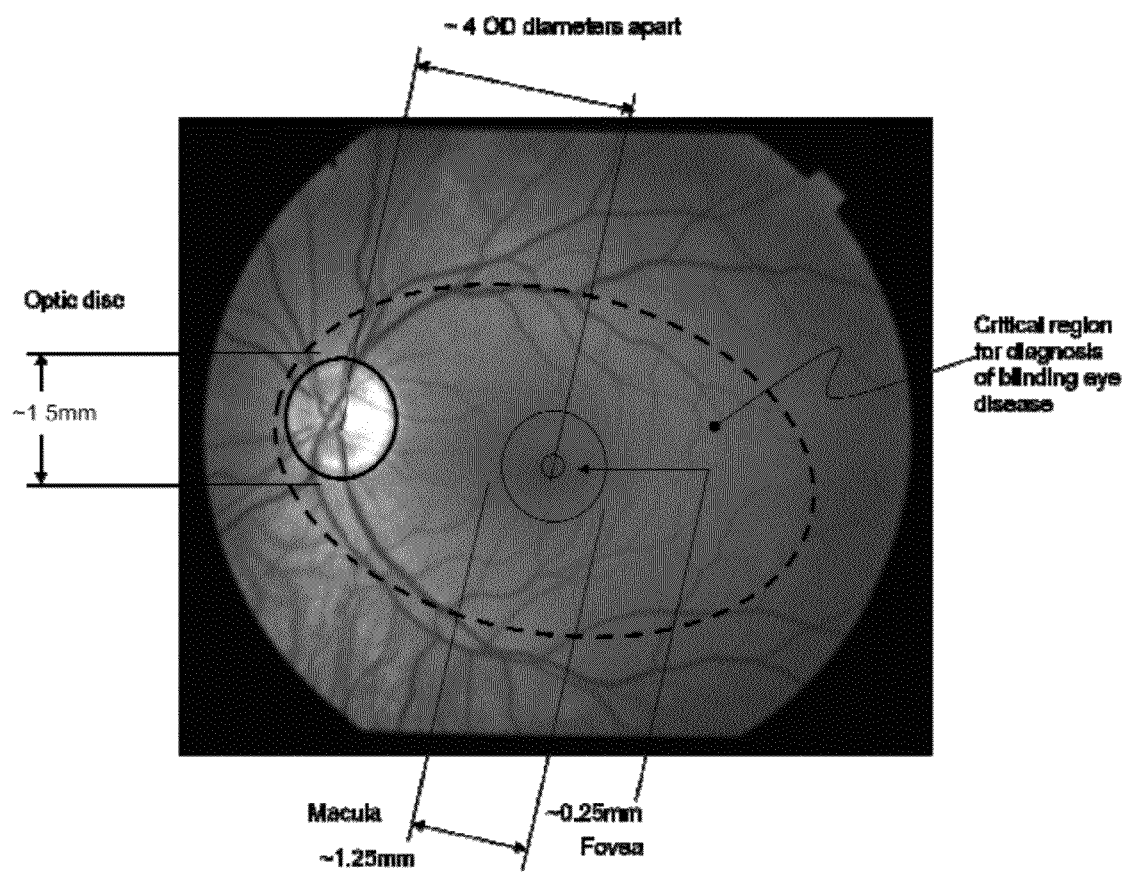
FIG. 3 shows a scanned image of a retina showing its major structures including macula and optic disc regions, as well as their relative scales.

FIG. 3 shows a scanned image of a retina showing major structures including macula and optic disc regions, as well as their relative geometric scales. As described earlier, the invention operates by analyzing and identifying, through image processing, critical structures of the retina that include and surround the macula and optic disc regions. Morphological or pigmentation changes in these regions, along with the presence of lesions such as drusen, exudates, dot hemorrhages, cotton wool spots, etc., have been found to be key indicators of the onset or progression of blinding eye disease. The computer analysis method further describes these regions and structures according a series of statistical feature vectors. These feature vectors are used to index the patient data in the CBIR system.

The CBIR aspects of the present invention only generally require that at least one image (more generally a plurality of images) with similar visual characteristics to that of an undiagnosed query image be found in the archive. Automated diagnosis according to the invention is made possible based on the finding that a similar process or phenomena likely generates images that are visually similar. This principle is applied herein to medical diagnostics of retinal imagery. The diagnosis is thus made indirectly based on the characterization of disease in the retrieved population (from the archive) according defined categories, such as the two level categories provided above.

Figure 4:
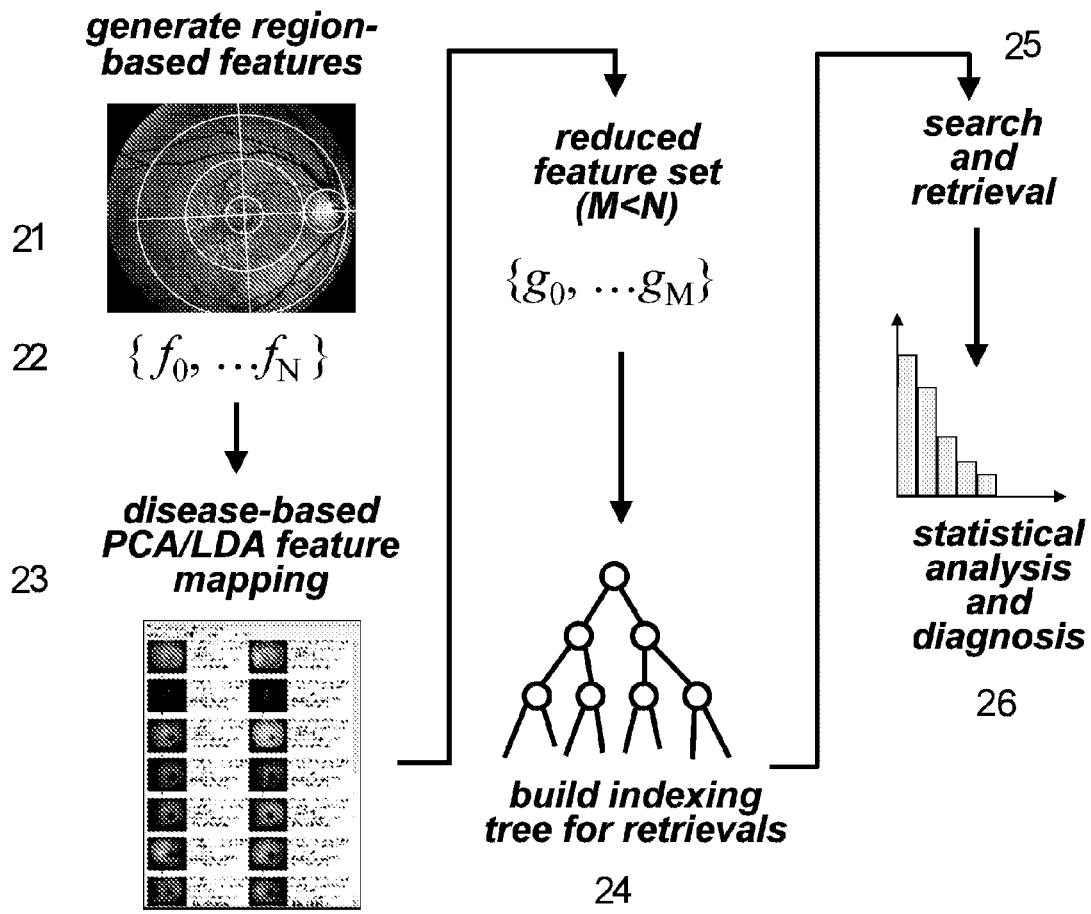
FIG. 4 shows specific details of one embodiment of the invention showing the inventive method comprising steps, steps 1 to 6.

Specific details of one embodiment of the invention is provided in FIG. 4. The method is shown as comprising six steps, steps 1 to 6.

Step 1. A digital retinal image is collected from a patient and automatically characterized to locate the vascular arcades, optic disc and macula regions. From this characterization, a macular coordinate system is imposed 21 such that the spatial positioning of disease-based morphological changes, location of lesions, etc., can be described in relation to the position of the macula and optic disc.

Step 2. Statistical features (shown as feature vectors, $f_0$ to $f_{N'}$) are extracted 22 from the salient regions of the retina which describe: (a) detected lesions such as drusen, exudates, cotton wool spots, dot hemorrhages, etc., (b) lesion statistics by category, e.g., moments, total counts, radial or annular distributions surrounding the macula center, etc., (c) oriented textures from the macula region, e.g., Gabor or Wald features, etc, and (d) features of the vascular arcade that describe shape, density, symmetry, etc.

Step 3. Apply principle component analysis (PCA) and linear discriminant analysis (LDA) to provide a mapping from a large feature vector set to a short, directed feature vector set 23. PCA and LDA methods are used to increase the discriminating power of a reduced feature set while mitigating feature redundancy, noise, and length. This step provides for a simplified content-based indexing architecture that allows images to be described in terms of the image content represented by an exemplar library, as opposed to the potentially complex feature structure used to represent the original images. By applying the PCA/LDA method, it is not uncommon to map an extensive feature set (e.g., >500 features) to a very succinct and discriminating subset (e.g., <50 features). This reduced-length feature vector becomes the index for each image in the database. This results in a more efficient Approximate Nearest Neighbor (ANN) search process in terms of both retrieval performance (e.g., precision) and the speed of retrieval.

In adapting the directed indexing method to retinal diagnostics, the user generally defines a directed indexing library (DIL) that contains exemplars of different categories of disease or that represent the variation of pathology associated with a particular disease state. For example, a DIL may be constructed that contains examples of early phase background DR as one category, proliferative DR as another category, age-related macular degeneration as another, and cystoid macular edema as yet another category. Each row of the DIL will contain examples of each particular category of interest. This will be established prior to building an indexing structure for the diagnostic CBIR system. The DIL will then be used to map the high-dimensional features of the original image regions to a lower dimensional feature space that focuses on the problem of retinal pathology characterization. The derived feature mapping is then applied to all future image content that enters the system. This method provides a method of mapping user semantics (i.e., meaning in the data) to the extracted features therefore matching user expectations to retrieval and therefore diagnostic performance, i.e., mitigating the semantic gap issue in CBIR systems.

Step 4. Using the CBIR method disclosed in U.S. Pat. No. 6,535,776 to Tobin, Jr. entitled "Method for localizing and isolating an errant process step", an indexing tree is built 24 with an Approximate Nearest Neighbor (ANN) method for efficient retrievals using the reduced feature vector for each patient record stored in the archive.

Step 5. Retrievals are then performed by formulating a query with an undiagnosed patient 25. The query is submitted to the CBIR system and a population of N visually similar images are returned, where N is a dynamic number $\geq 1$ determined by establishing a similarity threshold, T, using a suitable similarity metric (e.g., the population of images i=1, 2, . . . N, for which similarity is ~T). In the embodiment used in initial tests performed, the metric, $Si(Q,v_i)=1-d(Q,v_i)/\sqrt{M}$, where M is the number of features used (i.e., the dimension of the feature space) to describe the retinal imagery and i=1, 2, . . . N, being the size of the population of visually similar images for which $Si(Q,)\sim T$, and $d(Q,v_i)$ is a Euclidean of generalized L-norm distance function.

Step 6. Once a population of visually similar image data is returned containing N records, a statistical analysis is performed on the entire population or a sub-population to determine the prevalence of various disease states based on the frequency of occurrence 26. Subpopulations can be formed according to the patient gender, race, age, or other medical facts stored in the database archive. It is important that a large population of diagnosed and indexed patient data exist in the image archive to ensure statistical significance and uniformity across the registered disease types, gender, race, age, etc., in the system. Automatically performing a medical diagnosis based on a data archive attached to a content-based indexing of a large human patient population is a unique attribute of the present invention.

The invention can also be used to assess progression of retinal disease or diseases having retinal ramifications in a specific patient over a period time. As described above, The general CBIR method according to the invention permits evaluation of disease state using an archive of stored images with associated diagnosis and assessing the relative similarity of an unknown image to that library of images to obtain a diagnosis. However, once established as a population screening tool, the database, such as a Health Insurance Portability and Accountability Act (HIPAA) compliant database, of images from each patient can be established and the CBIR algorithm can be used to find and compare a retinal image to an image taken of the eye(s) of the same patient at one or more earlier points in time (e.g. years before). This embodiment provides assessment of progression of disease for patients as well as disease status relative to the archive.

For a very large patient population, as would be expected to be developed over a long time period from multiple sources of input such as through a web-based national subscription and submission system, it would be advantageous to reduce redundancy of image content in the database. For this purpose, an indexed data library that minimizes redundancy and provides a more uniform distribution of patient cases would be desirable.

In one embodiment, a method of increasing information content for content-based image retrieval (CBIR) systems comprises the step of providing a CBIR database, the database comprising an index for a plurality of stored digital images using a plurality of feature vectors. The feature vectors correspond to distinct descriptive characteristics of the images. A visual similarity parameter value is calculated based on a degree of visual similarity between feature vectors of an incoming image being considered for indexing into the database and feature vectors associated with a most similar of the images stored in the associated system. Based on the calculated visual similarity parameter value, it is determined whether to store or how long to store the feature vectors of the incoming image in the database.

The visual similarity parameter can be based on a distance, divergence or other information-theoretical comparison. Distances can include Minkowski-form distances, such as Euclidean or L-norm, or Mahalanobis or quadradic form distance. The divergences can include a Kullback-Leiber or Jeffrey divergence. In a preferred embodiment, the method further comprises the step of defining a threshold value, wherein if the visual similarity parameter value is above the threshold value the feature vectors associated with the incoming image is denied entry into the database, and if the similarity parameter value is less than the threshold the feature vectors of the incoming image is entered into the database. A plurality of threshold values can be defined, wherein the plurality of threshold values are used to define ranges of the similarity parameter values which are paired with durations for storage lifetimes in the database for the feature vectors of the incoming image.

Principal benefits of the present invention include the following:

1. A method for rapidly and automatically analyzing retinal imagery to provide a reliable diagnosis in a fraction of the time required by the reading center model currently in use in 2006.
2. An ability to provide an inexpensive, high-throughput retina analysis (and diseases having retinal manifestations) and diagnosis method and system for use in rural areas throughout the world (including the U.S. and in third-world countries) where medical opthalmology and other health care expertise is limited.
3. A method for making productive use of the historical record of digital fundus imagery that is being collected by the medical community today including red-free fundus imagery, imagery collected by non-mydriatic cameras, fluorescein angiography, and optical coherence tomography.
4. A method to provide the large organizations, such as the U.S. military, with the capability to perform rapid and accurate near real-time retinal scans on large numbers of personnel. In the case of the U.S. military, the invention can be used for personal in the service (e.g., abroad) and through the Veterans Administration with highly efficient throughput.

As noted above, although described relative to diagnosing retinal pathologies, the invention can be applied to other automated diagnosis scenarios based on other modes of biomedical imagery. For example, the invention can be used in conjunction with various imaging modalities including computed tomography (CT), positron emission CT (PET), single photon emission CT (SPECT), magnetic resonance imaging (MRI), and cellular oncology. The invention thus can be used to detect a broad range of diseases and abnormalities including various forms of cancer.

It is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains.

We claim:

1. A method for diagnosing medical conditions having retinal manifestations, comprising the steps of:
    providing a CBIR system including an archive of stored digital retinal photography images and diagnosed patient data corresponding to said retinal photography images, said stored images each indexed in a CBIR database using a plurality of feature vectors, said feature vectors corresponding to distinct descriptive characteristics of said stored images, and said diagnosed patient data identifying at least one of a plurality of disease states and one of one or more severity levels for the one of the plurality of disease states;
    obtaining a query image of the retina of a patient;
    identifying using image processing a plurality of separate regions or structures in said query image;
    describing said regions or structures using said plurality of feature vectors;
    retrieving a population of stored images from said database based on similarity to said regions or structures, and
    diagnosing a disease having retinal manifestations in said patient by:
        statistically analyzing said diagnosed patient data for said population to determine ones of the plurality of disease stated in said population and a prevalence of the ones of the severity levels corresponding to the ones of the plurality of disease states in said population,
        determining the absence or presence of a disease state in the patient based on the ones of the plurality of disease states in said population, and,
        if a disease state is present in the patient, a severity level of the disease state present in the patient based at least on a prevalent one of the severity levels corresponding to the ones of the plurality of disease states in the population associated with the present disease state.

2. The method of claim 1, wherein said regions or structures include normal physiologic and anomalous pathologic regions or structures.

3. The method of claim 2, wherein said anomalous regions are selected on the basis of spectral content, textures, structures, or shapes.

4. The method of claim 1, wherein said query image includes vascular arcades, macula, and optic disc and surrounding regions.

5. The method of claim 4, wherein said identifying step comprises imposing a macular coordinate system such that the spatial positioning of disease-based morphological changes or location of lesions is described in relation to a position of said macula and said optic disc.

6. The method of claim 4, wherein said obtaining step comprises:
    automatically locating said optic disc and said macula regions;
    imposing a macular coordinate system after automatic localization of center of said macula in said image, and
    describing spatial positioning of disease-based morphological changes in relation to a position of said macula and said optic disc.

7. The method of claim 1, wherein said database includes non-image data other than said diagnosed patient data, selected from the group consisting of age, race, gender, and medical history data for said patient.

8. The method of claim 1, wherein said feature vectors are indexed using an unsupervised clustering method into a hierarchical search tree.

9. The method of claim 1, wherein said diagnosed patient data is provided by a retinal professional.

10. The method of claim 1, wherein said method is entirely automatic.

11. The method of claim 1, wherein at least a portion of said digital retinal photography images are obtained at a remote location.

12. The method of claim 1, further comprising the step of increasing information content for said system, wherein said increasing information content comprises the steps of:
- calculating a visual similarity parameter value based on a degree of visual similarity between features vectors of an incoming image being considered for entry into said database and feature vectors of a most similar of said plurality of stored images in said database, and
- determining whether to store or how long to store said feature vectors associated with said incoming image in said database based on said visual similarity parameter value.

13. The method of claim 12, wherein said visual similarity parameter is based on a Euclidean distance or an L-norm distance.

14. The method of claim 12, further comprising the step of defining a threshold value, wherein:
- if said visual similarity parameter value is above said threshold value said incoming image is denied entry into said database, and
- if said similarity parameter value is less than said threshold said incoming image is entered into said database.

15. The method of claim 1, wherein said disease comprises an eye-disease.

16. The method of claim 1, wherein said disease comprises a non-eye disease.

17. The method of claim 1, wherein said archive of digital retinal photography images includes retinal images of said patient, wherein said method comprises the steps of:
- comparing said query image to retinal images of said patient in said archive, and assessing the progression of said disease for said patient.

18. The method of claim 1, wherein said statistical determination includes identifying a sub-population of said population based on one or more of patient gender, race or age.

19. A system for diagnosing diseases having retinal manifestations, comprising:
- computer apparatus programmed with a routine set of instructions stored in a fixed medium, said computer apparatus comprising:
  - a CBIR system including an archive of stored digital retinal photography images and diagnosed patient data corresponding to said retinal photography images, said stored images each indexed in a CBIR database using a plurality of feature vectors, said feature vectors corresponding to distinct descriptive characteristics of said stored images, and said diagnosed patient data identifying at least one of a plurality of disease states and one of one or more severity levels for the one of the plurality of disease states;
  - structure for obtaining a query image of the retina of a patient;
  - structure for identifying using image processing a plurality of separate regions or structures in said query image;
  - structure for describing said regions or structures using said plurality of feature vectors;
  - structure for retrieving a population of stored images from said archive based on similarity to said regions or structures, and
  - structure for diagnosing a disease having retinal manifestations in said patient by:
    - statistically analyzing said diagnosed patient data for said population to determine ones of the plurality of disease states in said population and a prevalence of the ones of the severity levels corresponding to the ones of the plurality of disease states in said population,
    - determining the absence or presence of a disease state in the patient based on the ones of the plurality of disease states in said population, and,
    - if a disease state is present in the patient, a severity level of the disease state present in the patient based at least on a prevalent one of the severity levels corresponding to the ones of the plurality of disease states in the population associated with the present disease state.

20. The system of claim 19, further comprising structure for implementing a clustering method to index said at least one feature vector in a hierarchical search tree.

* * * * *